(12) United States Patent
Downs, Jr.

(10) Patent No.: US 9,511,224 B1
(45) Date of Patent: Dec. 6, 2016

(54) BIONIC COCHLEA

(71) Applicant: Edward F. Downs, Jr., Lynn Haven, FL (US)

(72) Inventor: Edward F. Downs, Jr., Lynn Haven, FL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/532,891

(22) Filed: Nov. 4, 2014

(51) Int. Cl.
*A61N 1/00* (2006.01)
*A61N 1/36* (2006.01)
*A61N 1/375* (2006.01)
*H01L 41/113* (2006.01)

(52) U.S. Cl.
CPC ........... *A61N 1/36032* (2013.01); *A61N 1/375* (2013.01); *H01L 41/113* (2013.01)

(58) Field of Classification Search
USPC ............................................... 607/36, 56–57
See application file for complete search history.

(56) References Cited

U.S. PATENT DOCUMENTS

2007/0225776 A1* 9/2007 Fritsch ................ A61N 1/0541
607/57

* cited by examiner

*Primary Examiner* — Nicole F Johnson
(74) *Attorney, Agent, or Firm* — James T. Shepherd (57) ABSTRACT

A bionic cochlea includes a fluid filled vessel having a flexible window disposed in one of its walls. The flexible window flexes when exposed to an acoustic pulse to produce an acoustic pressure pulse in the fluid inside the vessel. A plurality of piezoelectric nanowires is disposed within the fluid filled vessel. The piezoelectric nanowires vibrate in response to acoustic pressure pulses transmitting through the fluid and produce electrical signals. Electrical wires in communication with the piezoelectric nanowires receive the produced electrical signals and pass these signals to the mammalian auditory nerve.

19 Claims, 8 Drawing Sheets

BIONIC COCHLEA

STATEMENT OF GOVERNMENT INTEREST

The invention described herein may be manufactured and used by or for the Government of the United States of America for Governmental purposes without the payment of any royalties.

BACKGROUND OF INVENTION

1) Field of the Invention

The present invention is directed to acoustic sensors as bionic cochlea.

2) Description of Prior Art

The most widely used prosthetic hearing device for deaf persons is the Cochlear implant (CI). The CI is an electronic device that uses conventional electronics and microphones to generate electrical signals that are fed into the damaged cochlea. The CI uses a stimulator implanted under the skin in combination with a battery powered microphone and processing electronics located outside the body. The two are attached together by a magnet. Sound waves detected by the external CI system are converted into electrical signals transmitted across the skin to the inner stimulator. The inner stimulator feeds electric signals inside the cochlea. Cochlear implants provide limited hearing to patients. The quality of sound is significantly different from a normal cochlea with less sound information being received and processed by the brain. Cochlear implants differ from hearing aids because they feed electrical signals to the auditory nerve inside the cochlea rather than amplifying sound and feeding the amplified sound to the ear drum.

In general, acoustics sensors use some type of transducer or microphone to sense acoustic energy, e.g., voice, music and vibrations. Air and contact, e.g., bone conduction, microphone elements utilize piezoelectric materials such as ceramic disk or polyvinylidene fluoride (PVDF) films. In a ceramic disk microphone, the ceramic disk is generally round and is glued to a thin metal substrate such as brass. The center of the disc is positive while the brass substrate is negative. In a PVDF film microphone, the PVDF film is either mounted to a metal, plastic or polymer substrate or is stretched over the open end of a cylinder so the film can vibrate freely.

Air microphones do not work well in high-noise environments as they pick up ambient noise along with any acoustic signals of interest. Bone conduction microphones are used in communication systems for the transmission of speech. When a person speaks, the cranial bones vibrate in accordance with the sounds that are produced by the vocal cords. Bone conduction microphones detect vibrations in the cranial bones and convert these vibrations to electrical signals that are fed into a two way radio. Bone conduction microphones are very useful in high-noise environments, but must firmly press against the bones in the skull in order to consistently detect vibrations. Over time, a bone conduction microphone becomes uncomfortable because of the constant pressure on a person's head.

Therefore, an acoustic sensor is desired that can be used as a bionic cochlea and that overcomes the poor sound quality of a CI and that avoids the problems with current air and contact microphones.

SUMMARY OF THE INVENTION

Exemplary embodiments in accordance with the present invention are directed to a bionic cochlea that replaces an existing human organic cochlea that is damaged due to trauma, disease, or birth defect, among other causes. The cochlea is the organ in the mammalian ear that converts sound energy into electrical energy. These electrical signals are fed to the brain through the auditory nerve. The bionic cochlea is inserted inside the skull, overcoming the performance issues associated with existing CI devices and eliminating infections that may occur with existing cochlear implants.

The organic cochlea includes cilia attached to the composite membrane to convert acoustic waves into electrical signals that feed into the auditory nerve. Exemplary embodiments of bionic cochlea in accordance with the present invention use piezoelectric nanowires attached to a composite basilar membrane to convert sound waves into electrical signals that feed into the auditory nerve. The piezoelectric nanowires convert acoustic pulses into electrical energy and are constructed from piezoelectric materials. Suitable piezoelectric materials include, but are not limited to, zinc oxide (ZnO), Polyvinylidene fluoride (PVDF), any other suitable organic or inorganic piezoelectric nanomaterial and combinations thereof. Preferably, the piezoelectric materials are PVDF and ZnO as these nano fibers have proven successful in harvesting energy from mechanical vibrations. Since the nanowires generate electrical energy when they are stimulated, the bionic cochlea does not require an external power source such as batteries.

In the mammalian auditory system, the structure of the ear is divided into three parts: the outer ear or pinna, the middle ear and the inner ear. The outer ear structure is responsible, in part, for helping locate sounds. In addition, this structure helps to funnel and focus sound waves to the middle ear. The middle ear contains the auditory canal, which terminates in the eardrum, or tympanic membrane. Attached to the opposite side of the eardrum from the auditory canal in a small air space are three tiny bones or ossicles, called the malleus, incus, and stapes (or hammer, anvil, and stirrup). These bones are attached to a fluid-filled spiral structure called the cochlea. The stirrup is attached to a point on the cochlea called the oval window. The eardrum and ossicles transfer sound waves to the cochlea. As the ossicles vibrate, they transfer sound energy to the cochlea. The cochlea includes three tapered tubes, which circle around like the scroll on a violin. The basilar membrane is located inside a central fluid filled tube called the scala media. The perception of sound takes place on the basilar membrane. The scala media is situated between two other fluid-filled tubes called the scala vestibuli and scala tympani which are joined at the tapered end of the cochlea.

The acoustic vibrations transmitted to the cochlea via the ossicles enter the cochlea via the oval window. The resulting pressure pulses travel down the scala vestibuli and scala tympani. As the pressure pulses travel inside the scala vestibuli and scala tympani, the pressure pulses are transferred to the scala media tube. In particular, the pressure pulse starts at the stirrup and travels down the scala vestibuli. This pulse causes the flexing of the Reissner's membrane that separates the scala vestibuli from the scala media. As the Reissner's membrane flexes, the tectorial membrane moves. The tectorial membrane rests on inner and outer hair cells attached to the organ of Corti. The inner hair cells produce electric energy as they move. The pressure pulse continues traveling inside the scale vestibuli into the scala tympani. The basilar membrane separates the scala tympani from the scala media. The pressure pulses in the scale tympani produce a flexing of the basilar membrane that causes the tectorial membrane to flex again thereby stimulating the inner hairs again.

The basilar membrane is a tapered structure. The narrow end, closest to the oval window is rigid and resonates at frequencies up to 25 KHz in human beings. At the distal end of the cochlea, the basilar membrane is wider and softer with a resonant frequency of 10 Hz. The basilar membrane is organized into octave bands. This is known as tonotopic organization and allows humans to better perceive and locate sound sources. The distance between acoustic pitch follows the same logarithmic distance as the perception of pitch. This is due to the fact that the octave bands on the basilar membrane are equidistant.

BRIEF DESCRIPTION OF THE DRAWINGS

It will he understood that many additional changes in details, materials, steps, and arrangements of parts which have been described herein and illustrated in order to explain the nature of the invention, may be made by those skilled in the art within the principle and scope of the invention as expressed in the appended claims.

DETAILED DESCRIPTION OF THE INVENTION

In the description which follows, any reference to either direction or orientation is intended primarily and solely for purposes of illustration and is not intended in any way as a limitation on the scope of the present invention. Also the particular embodiments described herein, although being preferred, are not to be considered as limiting of the present invention.

Figure 1:
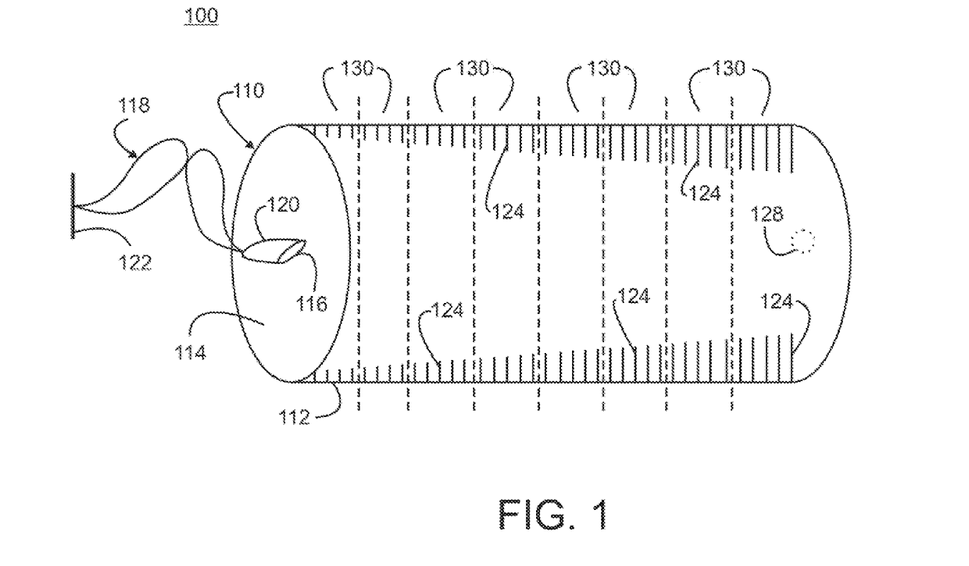
FIG. 1 is schematic representation of an embodiment of a bionic cochlea in accordance with the present invention.

Referring initially to FIG. 1, an exemplary embodiment of a bionic cochlea 100 in accordance with the present invention is illustrated. The bionic cochlea includes a fluid filled vessel 110 replicating the organic cochlea. The fluid filled vessel includes a plurality of walls defining a shape that accommodates insertion and placement inside a mammalian skull adjacent the ossicles or organic cochlea. Preferably, the fluid filled vessel is a cylindrical tube, having a circular cross section. The walls include the elongated cylinder 112 having a length and two circular ends 114.

The fluid filled vessel 110 can be filled with one or more of several fluids know in the art that are: (1) biocompatible; (2) sterile; and (3) preferably, have viscosities less than or equal to the viscosity of water, because higher viscosity fluids will hinder the propagation of sound waves (e.g., acoustic pressure pulses) within the fluid.

The bionic cochlea includes a flexible window 116 disposed in one of the walls of the fluid filled vessel 110. When the fluid filled vessel is a cylindrical tube, the flexible window is disposed in one of the circular ends. The flexible window flexes when exposed to an acoustic pulse to produce an acoustic pressure pulse in fluid located within the fluid filled vessel. Preferably, the flexible window is an oval window that easily flexes when an acoustic pulse impacts its surface. Suitable materials for the walls of the fluid filled vessel and the small thin flexible window include, but are not limited to biocompatible materials such as the silicone elastomer used to make breast implants or carbon fiber such as carbon nanotubes. If the fluid filled vessel 110 is made from a flexible biocompatible polymer, the flexible window 116 could be made of the same material but have less thickness that would allow it to flex locally more than the walls of the fluid filled vessel. Alternatively, if the fluid filled vessel is made of a solid, less flexible or nonflexible material, then the flexible window would preferably comprise a thin flexible biocompatible material as discussed above.

When the fluid filled vessel is inserted into the inner ear of the mammal, the oval window is placed in communication or contact with the ossicles 118 of the mammalian ear. In one embodiment, the oval window is in contact with the stapes 120. The stapes is disconnected from the oval window of the organic cochlea and mechanically fixed to the oval window 116 of the bionic cochlea. Suitable methods for attachment include, but are not limited to, a biocompatible adhesive such as used by barnacles to attach to ship hulls. When sound waves impact the biological ear drum 122 causing the ossicles to move, the stapes flexes the oval window of the bionic cochlea. This mechanical motion produces pressure waves that propagate through the fluid disposed inside the fluid filled vessel.

The bionic cochlea includes a plurality of piezoelectric nanowires 124 disposed within the fluid filled vessel. The plurality of piezoelectric nanowires acts like the cilia attached to the organ of Corti inside the bionic cochlea and vibrate in response to at least one predetermined wavelength in the acoustic pressure pulse transmitting through the fluid. This vibration produces an electrical signal.

In one embodiment, each piezoelectric nanowire 124 is a submicroscopic structure on the order of billionths of a meter in diameter. In addition to a nanowire, the base structure can be a nanotube or a nanobelt. The piezoelectric attributes of each nanowire are achieved by constructing each nanowire from piezoelectric materials or by making each nanowire of non-piezoelectric materials that have been doped with piezoelectric materials.

Suitable piezoelectric materials include, but are not limited to natural crystals such as berlinite, sucrose, quartz, rochelle salt, topaz, tourmaline-group minerals, and zinc oxide, manmade crystals such as gallium orthophosphate and langasite, manmade ceramics such as barium titanate, lead titanate, lead zirconate titanate (PZT), zirconate titanate potassium niobate, lithium niobate, lithium tantalate, sodium tungstate and boron nitride, piezoceramics such as sodium potassium niobate, bismuth ferrite and sodium niobate, polymers such as polyvinylidene fluoride (PVDF) and polydimethylsiloxane (PDMS), and combinations thereof.

One end of each piezoelectric nanowire is fixed and the opposite end is unattached, i.e., is free to move. In general, the length of each nanowire is tuned to vibrate when impinged by oscillating (acoustic) energy of interest. More specifically, this length is defined by the wavelength of a fundamental frequency of interest or one of the multiple harmonics or sub-harmonics thereof. In this way, the piezoelectric nanowire vibrates when subjected to acoustic energy having a wavelength that matches the predefined tuned length of the nanowire.

Figure 2:
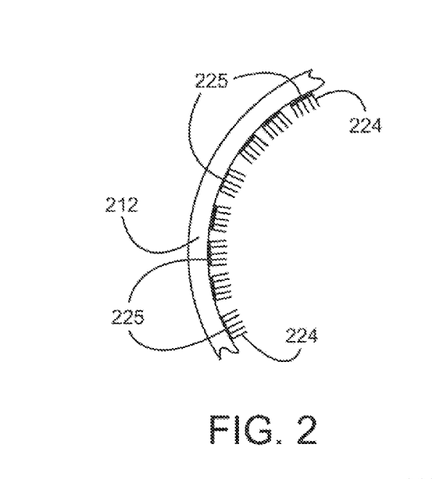
FIG. 2 is a partial view illustrating an embodiment of the piezoelectric nanowires and electric wires traces used in the bionic cochlea.

Vibrating piezoelectric nanowires generate electricity. Therefore, the bionic cochlea includes at least one electrical wire or electrical chase in communication with the plurality of piezoelectric nanowires to receive the electrical signals produced by the nanowires. Referring to FIG. 2, in one embodiment, the piezoelectric nanowires extend in from the walls of the fluid filled vessel. When the vessel is a cylindrical tube, the piezoelectric nanowires extend in from the interior surface of the elongated cylinder 212 portion along the length of the cylindrical tube. A plurality of wires 225 or wire traces run along the inside surface of the elongated cylinder, and a given group or set of the piezoelectric nanowires is in communication with or extends from each wire.

Figure 3:
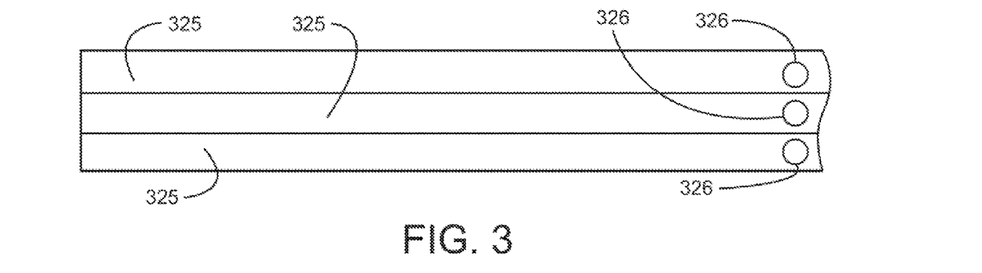
FIG. 3 is a schematic view of an embodiment of electric traces used in the bionic cochlea.

Referring to FIG. 3, each wire 325 can be spaced from the other wires or the wires can be arranged in parallel bands running along the length of the fluid filled vessel or cylindrical tube. Each electrical wire passes through the walls of the fluid filled vessel and is in communication with a mammalian auditory nerve.

In one embodiment, the electrical wires are attached to the interior surfaces of the walls of the fluid filled cylinder wall. Electrical traces are attached to the cylinder wall prior to depositing the nanowires. The traces carry electrical signals from the piezoelectric nanowires to the auditory nerve. As the pressure pulses travel through the fluid inside of the fluid filled vessel, these pressure pulses stimulate the piezoelectric nanowires along the walls of the fluid filled cylinder, producing electrical signals. In one embodiment, these signals are fed via the electrical wire traces to a nanopiezotronic semiconductor device. The output of the nanopiezotronic semiconductor device is attached to and in communication with the auditory nerves inside the organic cochlea inside the mammalian skull. Suitable materials and methods for making these connections are known and available in the art.

The nanopiezotronic, i.e., piezoelectric, semiconductor devices regulate the sound levels fed to the auditory nerve using an electrical bias provided to the semiconductor from the piezoelectric nanowires. The amplitude of the electrical signal levels fed into the auditory nerve are tunable so the sound perceived by the mammal is at a comfortable level. In one embodiment, the number of nanowires within the fluid filled vessel is adjusted to achieve the tunable amplitude. In another embodiment, a plurality of nanopiezotronic devices, i.e., piezoelectric semiconductor devices, 326 is used. One nanopiezotronic semiconductor device is used for each electrical wire. These devices act as acoustic limiters controlling the output levels from the piezoelectric nanowires and are powered by the same acoustic pulses stimulating the nanowires on the resonant membrane. The nanopiezotronic devices are mounted to the wire traces on the resonant membrane. The electrical signals from each group of piezoelectric nanowires associated with a given electrical wire are fed into the associated piezotronic junction gate field-effect transistor (JFET). The JFET output is fed to the auditory nerve.

Returning to FIG. 1, in the wall of the fluid filled vessel 110, or at the distal circular end of the cylindrical tube, is a small, thin round window 128. This window flexes as each pulse travels inside the fluid filled vessel. The round window relieves pressure inside the fluid filled vessel, preventing pressure spikes inside the fluid filled vessel as each pulse moves inside the fluid filled vessel. Pressure spikes can stimulate the piezoelectric nanowires to produce a false sound sensation. Round window 128 can be made of a similar material as the oval window 116, which would allow it to flex relative to the walls of the fluid filled vessel 110.

Exemplary embodiments of the bionic cochlea in accordance with the present invention are sensitive to oscillating energy over a range of frequencies. Accordingly, bionic cochlea in accordance with the present invention will utilize piezoelectric nanostructures having different lengths for sensitivity to oscillating energy over the frequency range of interest. The different length nanostructures can be provided on a single surface, substrate, or layer. However, multiple substrate layers may also be used.

In one embodiment, the plurality of piezoelectric nanowires attached to and extending from the interior surfaces of the walls of the fluid filled vessel is divided into a plurality of distinct octave bands 130. In one embodiment, these octave bands include a 25 KHZ band located adjacent the oval window 116 and a 10 Hz band disposed adjacent the round window 128. In one embodiment, the octave bands are centered at 25 KHz, 16 KHz, 8 KHz, 4 KHz, 2 KHz, 1 KHz, 500 Hz, 250 Hz, 125 Hz, 63 Hz, 31 Hz and 16 Hz. In one embodiment, the octave bands are positioned equidistant from each other as in an organic cochlea to create tonotopic organization that assists with sound location. The output from each octave band is fed into the electrical wires attached to the interior surface of the vessel wall. In one embodiment, these electrical wires feed into the nanopiezotronic semiconductors. Electrical wires carrying the output from the semiconductors are fed through the walls of the fluid filled vessel to the auditory nerve, for example, inside the organic cochlea.

In one embodiment, the piezoelectric nanowires are arranged in a linear fashion along the length of the vessel wall or cylindrical tube beginning with 25 KHz near the oval window and ending at 10 Hz near the round window. This arrangement does not divide the piezoelectric nanowires into octave bands. In one embodiment, at least about 32,000 piezoelectric nanowires are distributed along the length of the fluid filled vessel. Each piezoelectric nanowire has a distinct length. The shorter nanowires resonate at high frequencies, and the longer nanowires resonate at lower frequencies. This produces a linear distribution of nanowires along the length of the fluid filled vessel. Signals from the piezoelectric nanowires are collected on the electrical wires, fed into nanopiezotronic semiconductors and then communicated to the auditory nerve.

Figure 4:
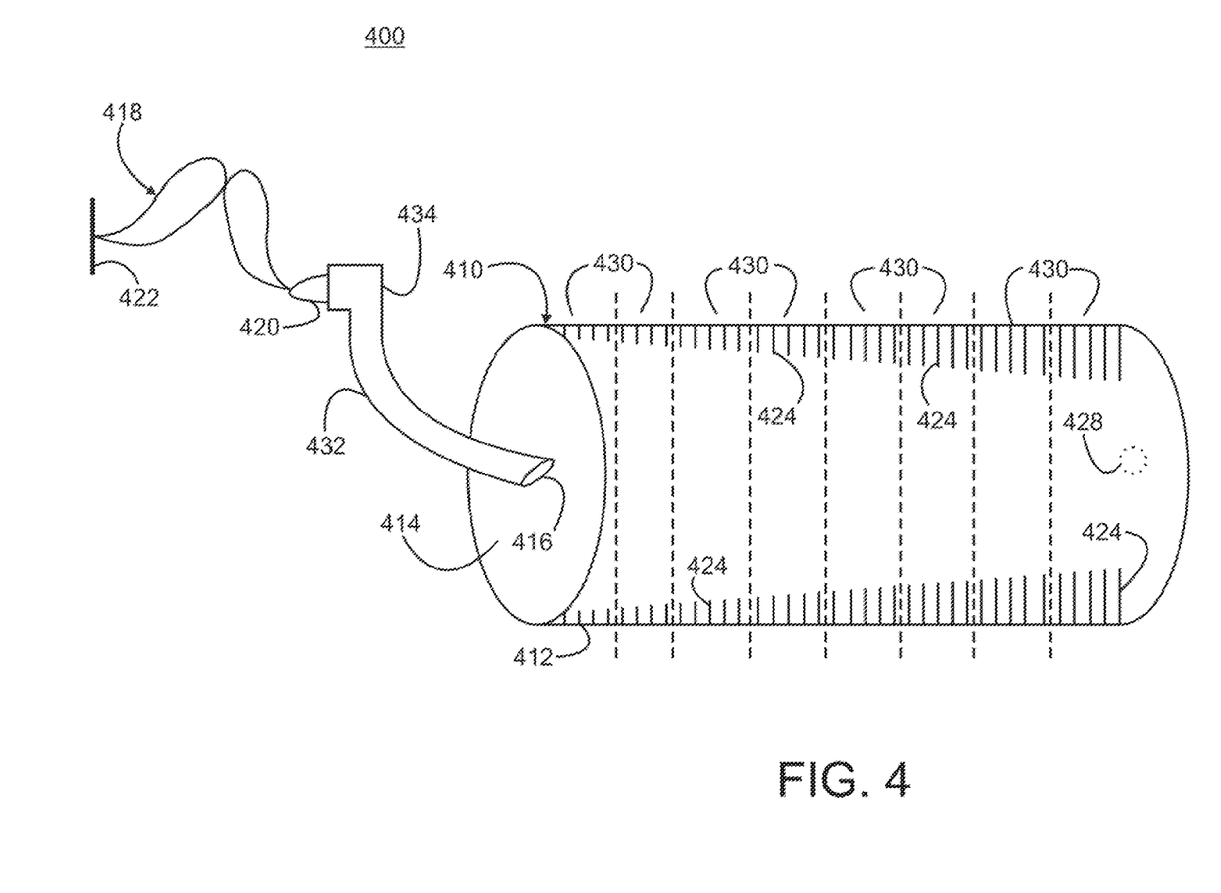
FIG. 4 is a schematic representation of another embodiment of a bionic cochlea having a thin flexible tube in accordance with the present invention.

Referring to FIG. 4, in another exemplary embodiment, the present invention is directed to a bionic cochlea 400 including a fluid filled vessel 410 arranged to be located behind the mastoid bone. The fluid filled vessel includes a plurality of walls defining a shape that accommodates insertion and placement inside a mammalian skull adjacent the ossicles 418 or organic cochlea. Preferably, the fluid filled vessel is a cylindrical tube, having a circular cross section. The walls include the elongated cylinder 412 having a length and two circular ends 414.

The bionic cochlea includes an open window 416 disposed in one of the walls of the fluid filled vessel. Preferably, the window is an oval window. Suitable materials for the walls of the fluid filled vessel include, but are not limited to, biocompatible materials such as the silicone elastomer used to make breast implants or carbon fiber such as carbon nanotubes.

In order to accommodate insertion behind the mastoid bone, the bionic cochlea includes a flexible fluid filled tube 432 in fluid connection with the fluid filled vessel. The flexible fluid filled tube 432 has a first end attached to the window 416 and a second end opposite the first end. The second end includes a thin diaphragm (not shown) that flexes when exposed to an acoustic pulse to produce an acoustic pressure pulse in the fluid inside the flexible fluid filled tube and the fluid filled vessel. Suitable materials for the flexible fluid filled tube and the thin diaphragm include, but are not limited to, biocompatible materials such as the silicone elastomer used to make breast implants or carbon fiber such as carbon nanotubes.

Fluid flows freely inside the thin wall flexible tube 432, and there is no diaphragm between the thin wall flexible tube and the fluid filled vessel, i.e., fluid can freely move between them. This allows pressure pulses to flow into the larger fluid filled vessel.

When the fluid filled vessel is inserted into the inner ear of the mammal, the diaphragm on one second end of the fluid filled flexible tube is placed in communication or contact with the ossicles 418 of the mammalian ear, for example between the incus and the stapes. In one embodiment, the diaphragm is in contact with the stapes 420. The stapes is disconnected from the oval window of the organic cochlea and mechanically fixed to the oval window 116 of the bionic cochlea. Suitable methods for attachment include, but are not limited to, a biocompatible adhesive such as used by barnacles to attach to ship hulls. When sound waves impact the biological ear drum 422 causing the ossicles to move, the stapes flexes the diaphragm. This mechanical motion produces pressure waves that propagate through the fluid disposed inside the fluid filled flexible tube and vessel.

In one embodiment, the flexible fluid filled tube 432 includes a rigid cylinder 434 extending in from the second end partially along a length of the flexible fluid filled tube. The rigid cylinder has a fixed bend comprising an angle of from about 30 degrees to about 90 degrees.

The bionic cochlea includes a plurality of piezoelectric nanowires 424 disposed within the fluid filled vessel. The plurality of piezoelectric nanowires acts like the cilia attached to the organ of Corti inside the bionic cochlea and vibrate in response to at least one predetermined wavelength in the acoustic pressure pulse transmitting through the fluid. This vibration produces an electrical signal.

In one embodiment, each piezoelectric nanowire 424 is a submicroscopic structure on the order of billionths of a meter in diameter. In addition to a nanowire, the base structure can be a nanotube or a nanobelt. The piezoelectric attributes of each nanowire are achieved by constructing each nanowire from piezoelectric materials or by making each nanowire of non-piezoelectric materials that have been doped with piezoelectric materials.

Suitable piezoelectric materials include, but are not limited to natural crystals such as berlinite, sucrose, quartz, rochelle salt, topaz, tourmaline-group minerals, and zinc oxide, manmade crystals such as gallium orthophosphate and langasite, manmade ceramics such as barium titanate, lead titanate, lead zirconate titanate (PZT), zirconate titanate potassium niobate, lithium niobate, lithium tantalate, sodium tungstate and boron nitride, piezoceramics such as sodium potassium niobate, bismuth ferrite and sodium niobate, polymers such as polyvinylidene fluoride (PVDF) and polydimethylsiloxane (PDMS), and combinations thereof.

One end of each piezoelectric nanowire is fixed and the opposite end is unattached, i.e., is free to move. In general, the length of each nanowire is tuned to vibrate when impinged by oscillating (acoustic) energy of interest. More specifically, this length is defined by the wavelength of a fundamental frequency of interest or one of the multiple harmonics or sub-harmonics thereof. In this way, the piezoelectric nanowire vibrates when subjected to acoustic energy having a wavelength that matches the predefined tuned length of the nanowire.

In the walls of the fluid filled vessel 410, or at the distal circular end of the cylindrical tube, is a small, thin round window 428. This window flexes as each pulse travels inside the fluid filled vessel. The round window relieves pressure inside the fluid filled vessel, preventing pressure spikes inside the fluid filled vessel as each pulse moves inside the fluid filled vessel. Pressure spikes can stimulate the piezoelectric nanowires to produce a false sound sensation. If the fluid filled vessel 410 is made from a flexible biocompatible polymer, the round window 428 could be made of the same material but have less thickness that would allow it to flex locally more than the walls of the fluid filled vessel. Alternatively, if the fluid filled vessel is made of a solid, less flexible or nonflexible material, then the round window 428 would preferably comprise a thin flexible biocompatible material as discussed above.

Exemplary embodiments of the bionic cochlea in accordance with the present invention are sensitive to oscillating energy over a range of frequencies. Accordingly, bionic cochlea in accordance with the present invention will utilize piezoelectric nanostructures having different lengths for sensitivity to oscillating energy over the frequency range of interest. The different length nanostructures can be provided on a single surface, substrate or layer. However, multiple substrate layers are also used.

In one embodiment, the plurality of piezoelectric nanowires attached to and extending from the interior surfaces of the walls of the fluid filled vessel is divided into a plurality of distinct octave bands 430. In one embodiment, these octave bands include a 25 KHz band located adjacent the oval window 416 and a 10 Hz band located the round window 428. In one embodiment, the octave bands are centered at 25 KHz, 16 KHz, 8 KHz, 4 KHz, 2 KHz, 1 KHz, 500 Hz, 250 Hz, 125 Hz, 63 Hz, 31 Hz and 16 Hz. In one embodiment, the octave bands are positioned equidistant from each other as in an organic cochlea to create tonotopic organization that assists with sound location. The output from each octave band is fed into the electrical wires attached to the interior surface of the vessel wall. In one embodiment, these electrical wires feed into nanopiezotronic semiconductors. Electrical wires carrying the output from the semiconductors are fed through the walls of the fluid filled vessel to the auditory nerve, for example, inside the organic cochlea.

In one embodiment, the piezoelectric nanowires are arranged in a linear fashion along the length of the vessel wall or cylindrical tube beginning with 25 KHz near the oval window and ending at 10 Hz near the round window. This arrangement does not divide the piezoelectric nanowires into octave bands. In one embodiment, at least about 32,000 piezoelectric nanowires are distributed along the length of the fluid filled vessel. Each piezoelectric nanowire has a distinct length. The shorter nanowires resonate at high frequencies, and the longer nanowires resonate at lower frequencies. This produces a linear distribution of nanowires along the length of the fluid filled vessel. Signals from the piezoelectric nanowires are collected on the electrical wires, fed into nanopiezotronic semiconductors and, then communicated to the auditory nerve.

Figure 5:
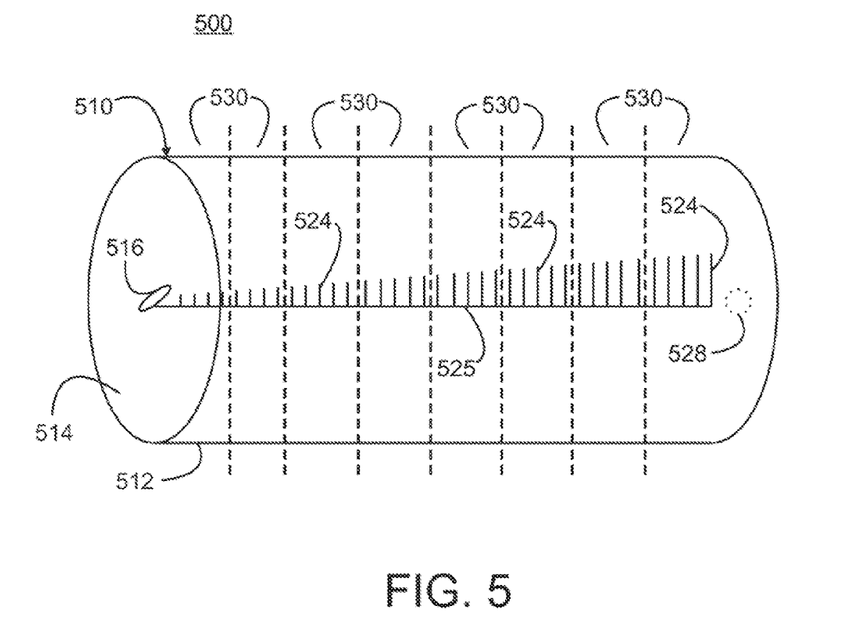
FIG. 5 is a schematic representation of another embodiment of a bionic cochlea having an internal flexible membrane in accordance with the present invention.

Referring to FIG. 5, another exemplary embodiment of a bionic cochlea 500 in accordance with the present invention is illustrated. The bionic cochlea includes a fluid filled vessel 510 replicating the organic cochlea. The fluid filled vessel includes a plurality of walls defining a shape that accommodates insertion and placement inside a mammalian skull adjacent the ossicles or organic cochlea. Preferably, the fluid filled vessel is a cylindrical tube, having a circular cross section. The walls include the elongated cylinder 512 having a length and two circular ends 514.

The bionic cochlea includes a flexible window 516 disposed in one of the walls of the fluid filled vessel 510. When the fluid filled vessel is a cylindrical tube, the flexible window is disposed in one of the circular ends. The flexible window flexes when exposed to an acoustic pulse to produce an acoustic pressure pulse in the fluid located within the fluid filled vessel. Preferably, the flexible window is an oval window that easily flexes when an acoustic pulse impacts its surface. Suitable materials for the walls of the fluid filled vessel and the small thin flexible window include, but are not limited to, biocompatible materials such as the silicone elastomer used to make breast implants or carbon fiber such as carbon nanotubes. If the fluid filled vessel 510 is made from a flexible biocompatible polymer, the flexible window 516 could be made of the same material but have less thickness that would allow it to flex locally more than the walls of the fluid filled vessel. Alternatively, if the fluid filled vessel 510 is made of a solid, less flexible or nonflexible material, then the flexible window 516 would preferably comprise a thin flexible biocompatible material as discussed above.

A flexible composite membrane 525 replicating the organic basilar membrane is disposed within the fluid filled vessel. Suitable materials for the flexible membrane include, but are not limited to, biocompatible materials such as a biocompatible silicone. In one embodiment, the flexible membrane 525 is positioned in the middle of the fluid filled vessel, running from the flexible window 516 to the thin round window 528. This round window 528 flexes as each pulse travels inside the fluid filled vessel. The round window 528 relieves pressure inside the fluid filled vessel, preventing pressure spikes inside the fluid filled vessel as each pulse moves inside the fluid filled vessel. Pressure spikes can stimulate the piezoelectric nanowires to produce a false sound sensation. Round window 528 can be made of a similar material as window 516, which would allow it to flex relative to the walls of the fluid filled vessel 510.

The bionic cochlea includes a plurality of piezoelectric nanowires 524 disposed within the fluid filled vessel and extend from at least one side of the flexible membrane. These piezoelectric nanowires act like the cilia inside the organic cochlea.

In one embodiment, the flexible membrane 525 and piezoelectric nanowires 524 are divided into a plurality of octave bands 530 starting with 25 KHz near the oval window 516 and ending with the 10 Hz band near the round window 528. In one embodiment, the octave bands are centered at the following frequencies: 25 KHz, 16 KHz, 8 KHz, 4 KHz, 2 KHz, 1 KHz, 500 Hz, 250 Hz, 125 Hz, 63 Hz, 31 Hz, 16 Hz. The octave bands are preferably positioned equidistant from each other like the bionic cochlea, creating tonotopic organization that assists with sound location.

Figure 6:
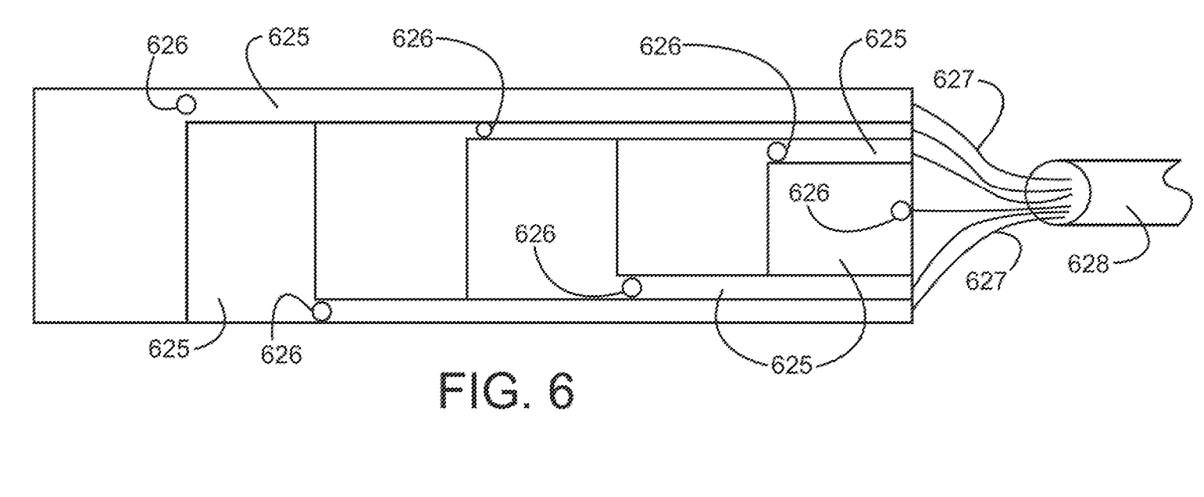
FIG. 6 is a schematic representation of an embodiment of wire traces attached to a side of the flexible membrane inside the bionic cochlea.

The bionic cochlea includes at least one, and preferably a plurality, of electrical wires in communication with the plurality of piezoelectric nanowires running along the flexible membrane to receive the produced electrical signals. The wires pass through the walls of the fluid filled vessel to be connected to the mammalian auditory nerve. Referring to FIG. 6, in one embodiment, the electrical wires are arranged as a plurality of wire traces 625 disposed on a side of the flexible membrane opposite the plurality of piezoelectric nanowires. In one embodiment, a single wire trace is provided for each one of the plurality of distinct octave bands, and the single wire trace is in communication with all of the piezoelectric nanowires in that octave band. Each wire trace is in contact with the wire lead 627 that is fed through the end of the fluid filled vessel into a wire bundle 628 that is attached to the mammalian auditory nerve, for example inside the organic cochlea.

In one embodiment the bionic cochlea includes a plurality of piezoelectric semiconductor devices 626. One nanopiezotronic semiconductor device is used for each electrical wire trace. As described above, these devices act as acoustic limiters controlling the output levels from the piezoelectric nanowires and are powered by the same acoustic pulses stimulating the nanowires on the resonant membrane.

In another embodiment, the flexible membrane includes a linear arrangement of tuned piezoelectric nanowires. These piezoelectric nanowires are attached to the composite membrane and are cut to resonant at octave and/or third octave bands. The resonant frequencies begin with 25 KHz near the oval window and end at 10 Hz near the round window. This arrangement differs from the first arrangement, because the wires are not divided into octave bands. Over 32,000 different resonant nanowires are distributed along the oscillating membrane. The shorter wires resonate at high frequencies and the longer wires resonate at lower frequencies. This allows a linear distribution of nanowires along the length of the flexible composite membrane. In one embodiment, electrical signals from the nanowires are collected on the electrical wires in separate bands attached to the back of each composite membrane, for example as illustrated in FIG. 6. These signals feed into nanopiezotronic semiconductor devices, and the output from the nanopiezotronic semiconductor devices feed into the auditory nerve.

Figure 7:
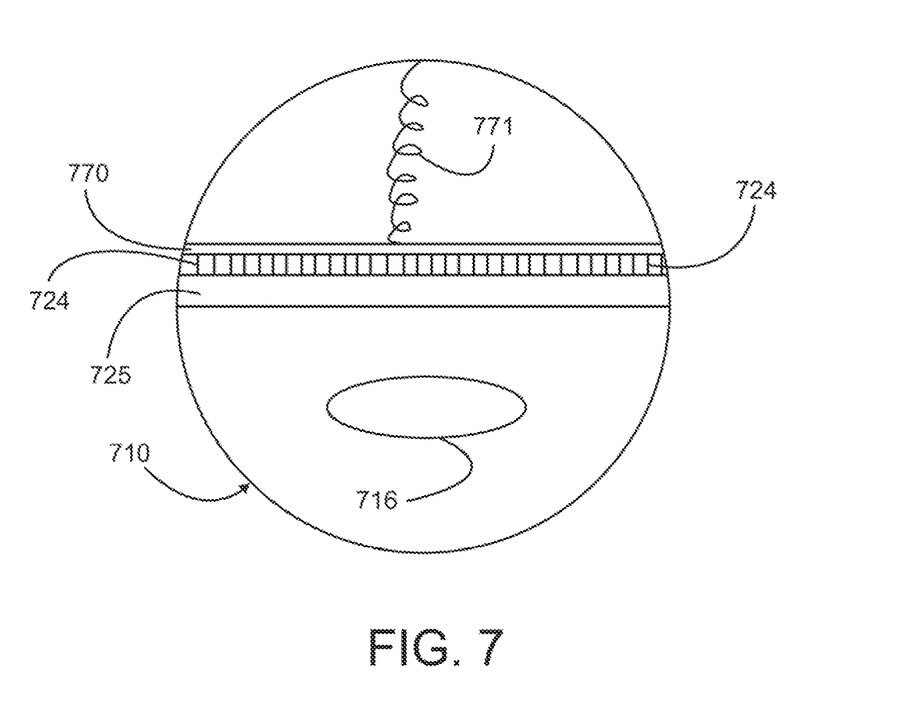
FIG. 7 is a schematic view of an embodiment of a bionic cochlea with an internal flexible membrane and internal semi-rigid membrane in accordance with the present invention.

In another embodiment, the piezoelectric nanowires are either divided into octave bands or arranged as continuous piezoelectric nanowires. Referring to FIG. 7, the flexible membrane 725 is very flexible and the bionic cochlea includes a semi-rigid membrane 770 resting on top of the piezoelectric nanowires 724 attached to the flexible membrane. Therefore the piezoelectric nanowires are located between the flexible membrane 725 and the semi-rigid membrane 770. To support the semi-rigid membrane, a flexible support member 771 extends from the semi-rigid membrane to a wall of the fluid filled vessel 710.

As an acoustic pulse enters into the fluid filled vessel via the oval window 716, the pressure pulse travels into the fluid filled cylinder 710, and the flexible membrane 725 flexes upward. The upward movement presses the nanowires into the semi-rigid membrane, causing the nanowires to flex and producing an electrical signal. The electrical signals flow along the electrical wires to the nanopiezotronic semiconductor devices.

Either a single or a plurality of semi-rigid membranes can be used. For example, a single semi-rigid membrane can be provided over each octave band of piezoelectric nanowires. For a continuous linear arrangement of piezoelectric nanowires, multiple semi-rigid membranes are positioned over the nanowires attached to the flexible membrane along the length of the fluid filled vessel.

Figure 8:
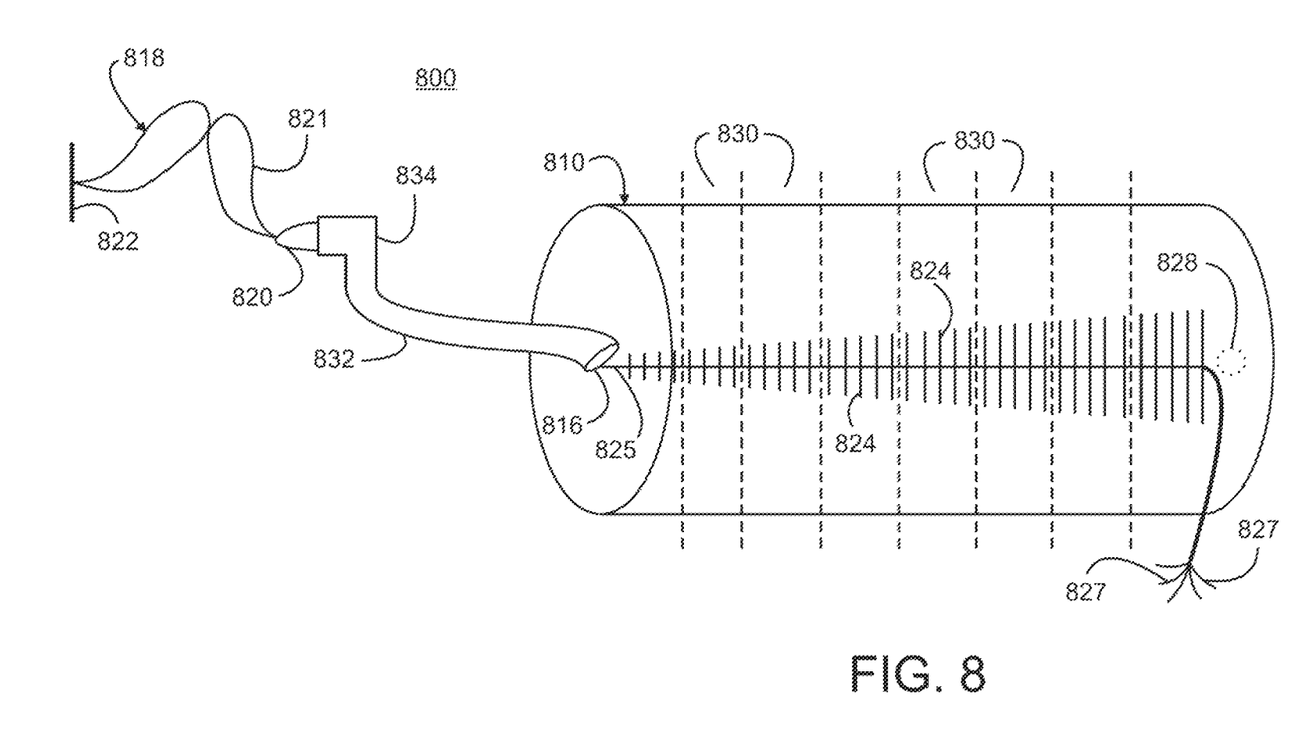
FIG. 8 is a schematic representation of another embodiment of a bionic cochlea having an internal flexible membrane and flexible tube in communication with the stapes in accordance with the present invention.
Figure 9:
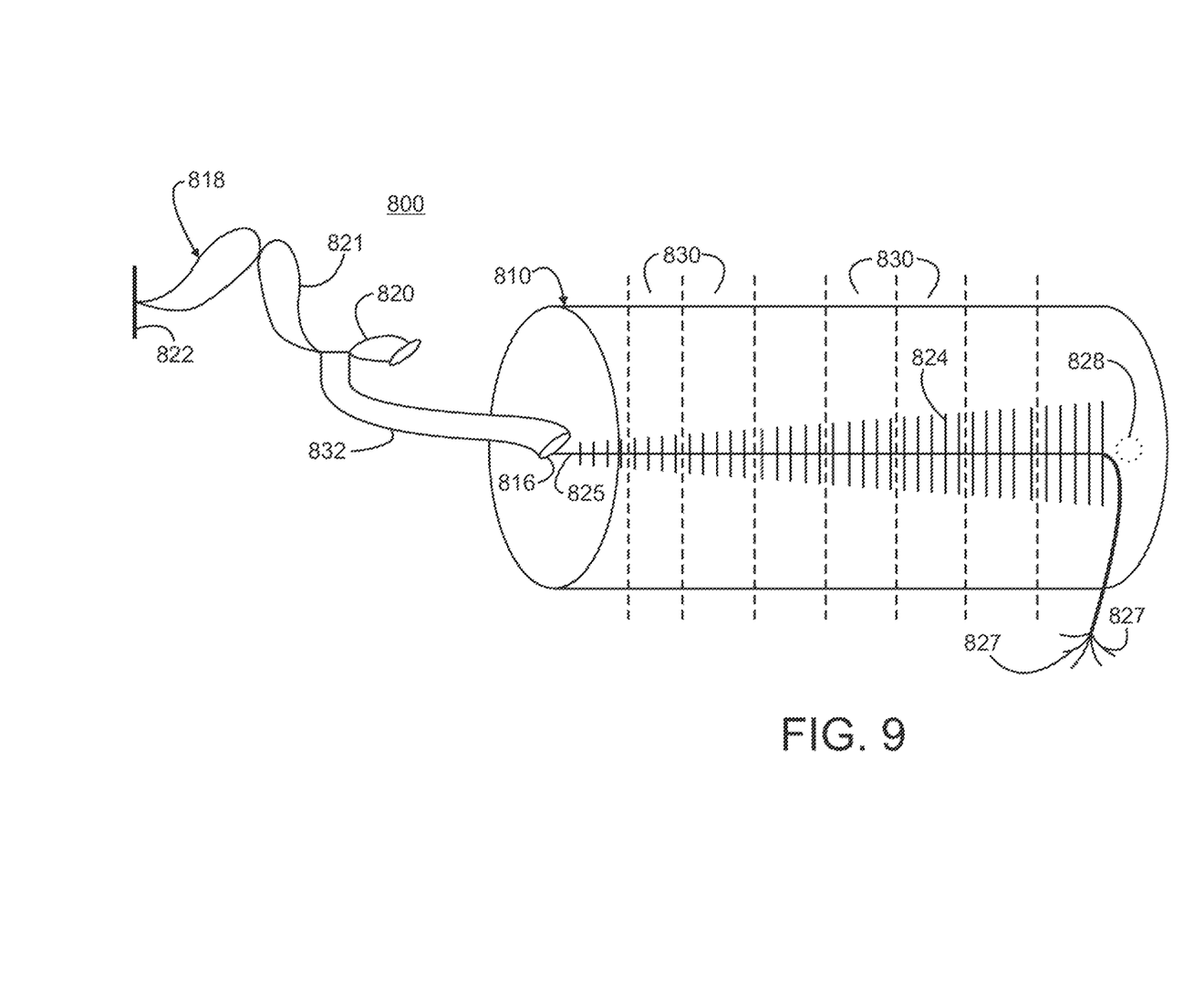
FIG. 9 is a schematic representation of another embodiment of a bionic cochlea having an internal flexible membrane and a flexible tube in communication between the stapes and the incus in accordance with the present invention.

Referring to FIG. 8, in another embodiment, the bionic cochlea 800 includes a fluid filled vessel 810 located behind the mastoid bone. This is facilitated by a thin flexible fluid filled tube 832 attached on a first end to the open oval window 816 of the larger fluid filled vessel 810 and on a second end is in communication with the ossicles 818 that move in response to pulses from the eardrum 822. For example, the second end is attached to the stapes 820 or is sandwiched between the incus 821 and stapes 820 (as shown in FIG. 9). Fluid flows freely inside the thin flexible tube, allowing acoustic pulses to travel through the thin flexible fluid filled tube into the larger fluid filled vessel. Acoustic pulses are generated when sound waves strike the ear drum 822.

The plurality of piezoelectric nanowires 824 are attached to both the first and second sides of the flexible membrane 825 running from the oval window 816 to the thin flexible window 828. The pressure pulses traveling into the fluid filled cylinder cause the piezoelectric nanowires to flex, generating electrical energy. The electrical signals travel along the electrical wires 827 to the mammalian auditory nerve, and may be routed through one or more nanopiezotronic semiconductor devices prior to traveling to the auditory nerve. Any piezoelectric nanowire configuration described above, including the division into a plurality of octave bands 830 can be used in this design. Also, flexible window 828 is made of a suitable material, as described above for the windows in the other embodiments, that would allow it to flex in response to acoustic pulses inside fluid filled tube 810.

There is no diaphragm between the thin wall tube 832 and the large fluid filled cylinder 810. This allows pressure pulses to flow freely into the large fluid filled cylinder. In one embodiment, to facilitate the transfer of pressure pulses from the stapes to the large fluid filled cylinder, a small rigid cylinder 834 bent at an angle of 30 to 90 degrees is attached to the and of the thin fluid filled tube 832 near the stapes 820. The end of the bent cylinder 834 near the stapes or between the stapes and incus is covered with a thin, flexible biocompatible silicone elastomer diaphragm (not shown). In one embodiment, the stapes is attached to the diaphragm using a biocompatible adhesive. As the ossicles and stapes vibrate, the diaphragm flexes producing acoustic pulses inside the fluid filled cylinder.

Hearing damage occurs when the cilia inside the organic cochlea are damaged either from mechanical trauma, drugs, or birth defect. To resolve this problem, the cilia can be replaced using the piezoelectric nanowires in accordance with the present invention. In one embodiment, the flexible membrane with the plurality of piezoelectric nanowires and electric wires is inserted into the organic cochlea. The piezoelectric nanowires act as the cilia, and the organic cochlea is the fluid filled vessel. Any one of the oscillating membranes covered with nanowires described above can be inserted into the existing organic cochlea. The electrical output from the nanowires are attached to the auditory nerve, and nanopiezoelectric JFETS are applied to the output of the nanowires just like they are in the fluid filled vessel embodiments described above. Once the membrane is inserted into the organic cochlea, the organic cochlea is closed. Hearing should be restored to a point where it equals or exceeds the original hearing.

These arrangements are superior to existing cochlear implants, because the piezoelectric nanowire cochlea arrangement eliminates the need for batteries or complex electrical circuits. In addition, the resulting bionic cochlea is completely implanted into the skull of a mammal, restoring hearing back to what was obtained using a standard organic cochlea. The frequency of the cochlea can be extended below 10 Hz and above 25 KHz.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly in combination with other embodiment(s). Therefore, it will be understood that the appended claims are intended to cover all such modifications and embodiments, which would come within the spirit and scope of the present invention.

What is claimed is:

1. A bionic cochlea comprising:
 an enclosed fluid filled vessel comprising walls, each of the walls having an interior surface;
 a flexible first window disposed in one of the walls, the material and thickness of the first window selected to flex locally relative to the walls of the fluid filled vessel when exposed to an acoustic pulse to produce an acoustic pressure pulse in the fluid inside the vessel;
 a plurality of piezoelectric nanowires disposed within the fluid filled vessel and extending from the walls of the fluid filled vessel, each of the nanowires having one end fixed to one of the interior surfaces and an unattached second end extending into the interior of the vessel, the length of each of the nanowires configured selected to vibrate in response to at least one predetermined wavelength in the acoustic pressure pulse, thereby producing an electrical signal; and
 at least one electrical wire in communication with the plurality of piezoelectric nanowires to receive the produced electrical signals.

2. The bionic cochlea of claim 1, wherein the fluid filled vessel comprises a cylindrical tube.

3. The bionic cochlea of claim 2, wherein the first window is disposed in an end of the cylindrical tube.

4. The bionic cochlea of claim 1, wherein at least one of the walls of the fluid filled vessel and the first window comprises a silicone elastomer.

5. The bionic cochlea of claim 1, wherein at least one of the walls of the fluid filled vessel and the first window comprise carbon fiber.

6. The bionic cochlea of claim 1, wherein the first window comprises an oval window.

7. The bionic cochlea of claim 1, wherein the first window is in communication with one of the ossicles of a mammalian ear.

8. The bionic cochlea of claim 7, wherein the one of the ossicles in communication with the first window is the stapes of a mammalian ear.

9. The bionic cochlea of claim 1, wherein the plurality of piezoelectric nanowires comprises zinc oxide.

10. The bionic cochlea of claim 1, wherein the plurality of piezoelectric nanowires comprises polyvinylidene fluoride.

11. The bionic cochlea of claim 1, wherein the plurality of piezoelectric nanowires are grouped into a plurality of distinct resonant frequency octave bands, each octave band comprising a set of piezoelectric nanowires centered on a distinct resonant frequency.

12. The bionic cochlea of claim 11, wherein the octave bands are centered on 25 KHz, 16 KHz, 8 KHz, 4 KHz, 2 KHz, 1 KHz, 500 Hz, 250 Hz, 125 Hz, 63 Hz, 31 Hz, and 16 Hz resonant frequencies.

13. The bionic cochlea of claim 11, further comprising a plurality of electrical wires, each electrical wire being in communication with the piezoelectric nanowires grouped in a corresponding octave band.

14. The bionic cochlea of claim 1, wherein the plurality of piezoelectric nanowires comprises a linear distribution of piezoelectric nanowires, each piezoelectric nanowire in the linear distribution having a distinct length and a distinct resonant frequency.

15. The bionic cochlea of claim 14, wherein the fluid filled vessel comprises a cylindrical tube and the linear distribution of piezoelectric nanowires is disposed along a length of the cylindrical tube.

16. The bionic cochlea of claim 1, wherein the bionic cochlea further comprises at least one nanopiezoelectric semiconductor in communication with the electric wire to regulate an amplitude of the produced electrical signals passing through the electric wire.

17. The bionic cochlea of claim 1, wherein the electrical wire is in communication with a mammalian auditory nerve.

18. The bionic cochlea of claim 1, further comprising a flexible second window disposed in one of the walls, the material and thickness of the second window selected to flex locally relative to the walls of the fluid filled vessel when exposed to the acoustic pressure pulse and relieve pressure inside the fluid filled vessel.

19. The bionic cochlea of claim 18, wherein the fluid filled vessel comprises a cylindrical tube, the first window is disposed in an end of the cylindrical tube, and the second window is disposed in the end of the cylindrical tube opposite the first window.

* * * * *